United States Patent [19]

Haralambidis

[11] Patent Number: 5,552,540
[45] Date of Patent: Sep. 3, 1996

[54] NUCLEOSIDE DERIVATIVES

[75] Inventor: Jim Haralambidis, Victoria, Australia

[73] Assignee: Howard Florey Institute of Experimental Physiology and Medicine, Victoria, Australia

[21] Appl. No.: 68,604

[22] Filed: May 27, 1993

Related U.S. Application Data

[63] Continuation of Ser. No. 457,747, filed as PCT/AU88/00207, Jun. 24, 1988, published as WO88/10264, Dec. 29, 1988, abandoned.

[30] Foreign Application Priority Data

Jun. 24, 1987 [AU] Australia ............... PI2666/87

[51] Int. Cl.$^6$ .................................. C07H 19/06
[52] U.S. Cl. .................. 536/25.34; 536/25.32; 536/26.8; 536/28.53; 536/28.54
[58] Field of Search ................ 536/26.7, 25.34, 536/28.53, 28.54, 28.55, 26.8, 26.6, 27.11

[56] References Cited

U.S. PATENT DOCUMENTS 4,711,955  12/1987  Ward et al. ................... 536/26.71
5,047,519   9/1991  Hobbs, Jr. et al. ............ 536/26.71

OTHER PUBLICATIONS

Langer et al., Proc. Natl. Acad. Sci. USA, vol. 78, No. 11 pp. 6633–6637, Nov. 1981.
Robins et al., Journal of Organic Chem., vol. 48, pp. 1854–1862, 1983.

Primary Examiner—Douglas W. Robinson
Assistant Examiner—James O. Wilson
Attorney, Agent, or Firm—Sughrue, Mion, Zinn, Macpeak & Seas

[57] ABSTRACT

A nucleoside derivative of formula (1), characterized in that: Y is H or OH or a protected hydroxy group; X is H, a phosphonate group or a phosphoramidite group of formula (II), where $R^1$ and $R^2$ are the same or different, and are selected from alkyl and substituted alkyl, which may be branched or unbranched; and Q is a phosphate protecting group; Z is H, a phosphate or triphosphate group or hydroxy protecting group; X' is a $C_{1-15}$ alkyl group which may be branched or unbranched; R is an amino protecting group or a fluorophore, or other non-radioactive detectable marker; or the group Y'NHA, where Y' is an alkyl ($C_{1-40}$) carbonyl group which may be branched or unbranched, and A is an amino protecting group or a fluorophore or other non-radioactive detectable marker. Methods for the synthesis and sequencing of polynucleotides utilizing compounds of formula (I).

10 Claims, 8 Drawing Sheets

SALIVARY GLAND
LIVER
tRNA

SALIVARY GLAND
LIVER
tRNA

NUCLEOSIDE DERIVATIVES

This is a continuation of application Ser. No. 07/457,747, filed as PCT/AU88/00207 on Jun. 24, 1988, published as WO88/10264 on Dec. 29, 1988, now abandoned.

The present invention relates to nucleoside derivatives, methods for their synthesis, and methods for the synthesis and sequencing of polynucleotides utilizing such nucleoside derivatives.

[NOTE: References cited herein are collected at the end of the specification.]

DNA, synthetic oligonucleotides and RNA labelled with identifiable markers have found wide application in molecular biology.

Radioactive labels, such as $^{32}P$ and $^{35}S$ have been almost exclusively used in molecular biological procedures. Radioactive labels have the disadvantage, however, that their half life is relatively short (for example, the half life of $^{32}P$ is 14 days) and that the ionizing radiation emitted during their decay is capable of damaging cellular components such as proteins, lipids and nucleic acids, which may result in cell death, or transformation of cells to malignant forms.

It has been proposed to label nucleotides or oligonucleotides with non-radioactive markers such as fluorophores, colloidal compounds and enzymes.

In one proposed approach[1], oligonucleotides containing a reactive amino group at the 5' end were prepared. Fluorophores or other non-radioactive markers were then attached to the amino group to produce an oligonucleotide incorporating a detectable marker. Such an approach has the disadvantage that only a single detectable marker can be introduced into the oligonucleotide chain through its 5' end.

In another proposal[2-5], C-5 substituted deoxyuridine compounds have been prepared, which have an amino group at the far end of the C-5 substituent. Such compounds may be labelled with a detectable marker and may be incorporated into an oligonucleotide chain, thereby allowing an oligonucleotide to be labelled at multiple sites. The preparation of these compounds is difficult and involves reactions using highly toxic mercury derivatives.

There is thus a need for nucleoside derivatives which may be used in the production of non-isotopically labelled polynucleosides, and which may be simply and safely prepared.

According to the present invention there is provided a nucleoside derivative of the formula (I):

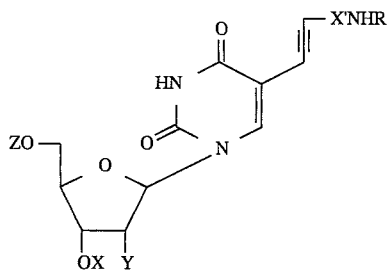 (I)

characterized in that;

Y is H or OH or a protected hydroxy group;

X is H, a phosphonate group or a phosphoramidite group of the formula

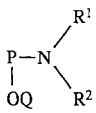

where $R^1$ and $R^2$ are the same or different, and are selected from alkyl and substituted alkyl, which may be branched or unbranched; and Q is a phosphate protecting group;

Z is H a phosphate or triphosphate group or a hydroxy protecting group;

X' is a $C_{1-15}$ alkyl group which may be branched or unbranched;

R is an amino protecting group or a fluorophore, or other non-radioactive detectable marker; or the group Y'NHA, where Y' is an alkyl ($C_{1-40}$) carbonyl group which may be branched or unbranched, and A is an amino protecting group or a fluorophore or other non-radioactive detectable marker.

For ease of discussion, FIG. 1, which depicts one preferred compound in accordance with the ivention, also shows the numbering system used in this specification for the C-5 substituted nucleosides.

We have found that C-5 substituted uridine and deoxyuridine, having a primary aliphatic amino group attached to, or capable of attachment to, a non-radioactive label, can be readily prepared under mild conditions, using a palladium catalysed C—C bond forming reaction between an aminoalkyne and 5-iodouridine or 5-iododeoxyuridine derivatives.

$R^1$ and $R^2$ may each contain from 1 to 30 carbon atoms. Preferably, $R^1$ and $R^2$ are both isopropyl groups. Where $R^1$ and/or $R^2$ are substituted alkyl, the nature of the substituents is unimportant providing the substituents do not interfere with the desired properties of the compound or have other deleterious effects. For example, the substituents may be selected from phenyl, benzyl and acyl groups.

Q may be any phosphate protecting group such as methyl, phenyl, substituted phenyl, benzyl or cyanoethyl groups. For example, phenyl may be substituted with halogen, hydroxy or nitro groups.

Any hydroxy protecting group, such as those described by Greene[6], may be employed. For example, hydroxy protecting groups may be selected from acyl such as substituted or unsubstituted alkanoyl (e.g. formyl, acetyl, propionyl, butyryl, isobutyryl, valeryl, bromoacetyl, dichloroacetyl, trifluoroacetyl), substituted or unsubstituted aroyl (e.g. benzoyl, toluoyl, xyloyl, nitrobenzoyl, bromobenzoyl, salicyloyl), arylalkyl (e.g. benzyl), methyl, methoxy, methylthiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl 2-(phenylselenyl)ethyl, t-buryl, allyl, benzyl, o-nitrobenzyl, triphenylmethyl, α-naphthyldiphenylmethyl, p-methoxyphenyldiphenylmethyl, 9-(9-phenyl-10-oxo)anthryl (Tritylone), dimethoxy trityl or pixyl, trimethylsilyl, isopropyldimethylsilyl, t-butyldi- methylsilyl, t-butyldiphenylsilyl, tribenzylsilyl, triisopropylsilyl.

Any amino protecting group such as those described by Greene[6], may be employed. For example, amino protecting groups may be selected from acyl, particularly organic acyl, for example, substituted or unsubstituted aliphatic hydrocarbonoxycarbonyl such as alkoxycarbonyl (e.g. methoxycarbonyl, ethoxycarbonyl, propoxycarbonyl, butoxycarbonyl, t-butoxycarbonyl, 5-pentoxycarbonyl), haloalkoxycarbonyl (e.g. chloromethoxycarbonyl, tribromoethoxycarbonyl, trichloroethorycarbonyl), an alkane- or arene- sulfonylalkoxycarbonyl (e.g. 2-(mesyl)ethoxycarbonyl, 2-(p-toluenesulonyl)ethoxycarbonyl), an alkylthio- or arylthioalkoxycarbonyl (e.g. 2-(ethylthio)ethoxycarbonyl, 2-(p-tolylthio)ethoxycarbonyl,), substituted or unsubstituted alkanoyl such as halo(lower)alkanoyl (e.g. formyl, trifluoroacetyl), a monocyclic or fusedcyclic-alicyclic oxycarbonyl (e.g. cyclohexyloxycarbonyl, adamantyloxycarbonyl, isobornyloxycarbonyl), substituted or unsubstituted alkenyloxycarbonyl (e.g. allyoxycarbonyl), substituted or unsubstituted alkynyloxycarbonyl (e.g. 1,1-dimethylpropargyloxycarbonyl), substituted or unsubstituted aryloxycarbonyl (e.g. phenoxycarbonyl, p-methylphenoxycarbonyl), substituted or unsubstituted aralkoxycarbonyl (e.g. benzyloxycarbonyl, p-nitrobenzyloxycarbonyl, p-phenylazobenzyloxycarbonyl, p-(p-methoxyphenylazo)benzyloxycarbonyl, p-chlorobenzyloxycarbonyl, p-bromobenzyloxycarbonyl, α-naphthylmethoxycarbonyl, p-biphenylisopropoxycarbonyl, fluorenymethoxycarbonyl), substituted or unsubstituted arenesulfonyl (e.g. benzenesulfonyl, p-toluenesulfonyl), substituted or unsubstituted dialkylphosphoryl (e.g. dimethylphosphoryl), substituted or unsubstituted diaralkylphosphoryl (e.g. O,O-dibenzylphosphoryl), substituted or unsubstituted aryloxyalkanoyl (e.g. phenoxyacetyl, p-chlorophenoxyacetyl, 2-nitrophenoxyacetyl, 2-methyl-2-(2-nitrophenoxy)propyonyl)

substituted or unsubstituted aryl such as phenyl, tolyl;

substituted or unsubstituted aralkyl such as benzyl, diphenylmethyl, trityl or nitrobenzyl.

The term "fluorophore" refers to a moiety which in itself is capable of fluoresence or which confers fluoresence on another moiety. As used in this specification the term "fluorophore" also refers to a fluorophore precursor which contains one or more groups which suppress fluoresence, but which is capable of fluoresence once these groups are removed. (For example, diisobutyryl 6-carboxy fluorescein is non-fluorescent. Treatment with ammonia removes the diisobutyryl groups to give fluorescent 6-carboxy fluorescein). Examples of fluorophores or fluorophore precursors:

fluoroscein-5-isothiocyanate acyl (for example: diisobutyryl, acetyl or dipivaloyl)-5-and/or 6-carboxy-fluorescein pentafluorophenyl ester, 6-(diaryl-5 and/or 6-carbonyl-fluorescein)aminohexanoic acid pentafluorophenyl ester, Texas Red (Trademark of Molecular Probes, Inc.), tetramethylrhodamine-5 (and 6) isothiocyanate (hereinafter referred to as rhodamine), eosin-5-isothiocyanate, erythrosin-5-isothiocyanate, 4-chloro-7-nitrobenz-2-oxa-1,3-diazole, 4-fluoro-7-nitrobenz-2-oxa-1,3-diazole, 3-(7-nitrobenz-2-oxa-1,3-diazol-4-yl) methylaminopropionitrile, 6-(7-nitrobenz-2-oxa-1,3-diazol-4-yl)aminohexanoic acid, succinimidyl 12-(N-methyl-N-(7-nitrobenz-2-oxa-1,3-diazol-4-yl)aminododecanoate, 7-diethylamino-3-(4'-isothiocyanatophenyl)-4-methylcoumarin (CP), 7-hydroxycoumarin-4-acetic acid, 7-dimethylaminocoumarin-4-acetic acid, succinimidyl 7-dimethylaminocoumarin-4-acetate, 7-methoxycoumarin-4-acetic acid, 4-acetamido-4'-isothiocyanatostilbene-2-2'-disulfonic acid (SITS), 9-chloroacridine, succinimidyl 3-(9-carbazole)propionate, succinimidyl 1-pyrenebutyrate, succinimidyl 1-pyrenenonanoate, p-nitrophenyl 1-pyrenebutyrate, 9-anthracenepropionic acid, succinimidyl anthracene-9-propionate, 2-anthracenesulfonyl chloride.

Preferably, the fluorophores or fluorogenic substances have the following spectroscopic properties:

(i) an excitation maximum coinciding with one of the strong emmission lines of the commercially used high pressure mercury lamps;

(ii) an emmission maximum in the visible part of the spectrum.

Non-radioactive detectable markers include entities which may be detected directly by their physical properties, such as electron dense materials which can be detected under a microscope; or entities which may be detected indirectly by their chemical or biochemical properties, such as by the reaction of the detectabler marker with a suitable substrate(s) to produce a detectable signal, such as colour. Examples of non-radioactive detectable markers which may be detected directly includes colloidal compounds such as colloidal gold and silver, and ferritin. Examples of non-radioactive detectable markers which may be detected indirectly include biotin, avidin and enzymes such as β-galactosidase, urease, peroxidase and alkaline phosphatase.

X' is preferably $CH_2$

R is preferably $CO(CH_2)_{1-15}$ A and more preferably $CO(CH_2)_5 A$.

Particularly preferred compounds of formula (I) have the following substituents:

| Y | X | Z | X' | R |
|---|---|---|-----|---|
| DH | $CH_3O-P(N(L)(L))$ | DMTr | $CH_2$ | $O-CH-(CH_2)_5NHA$ |
| H | " | DMTr | $CH_2$ | " |
| OH | H | DMTr | $CH_2$ | " |
| H | H | Triphosphate | $CH_2$ | " | where the group A is as defined above, and DMTr refers to dimethoxy trityl, and D is a hydroxy protecting group.

The compounds of the formula (1) maybe prepared by reacting a 5-iodouridine or 5-iododeoramridine of the formula:

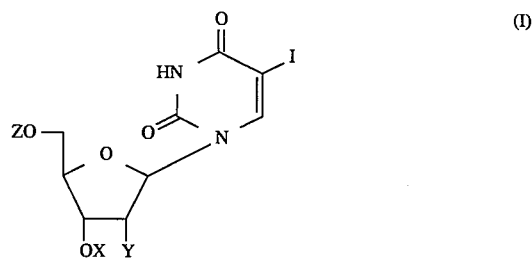

wherein X and Z are as previously defined in claim 1; with an aminoalkyne having the formula H—C≡CX'NR, where X' and R are as previously defined, in the presence of a palladium catalyst.

More particularly, compounds of the formula (I) may be prepared according to the following steps:

(A) Reacting a compound of the formula (1):

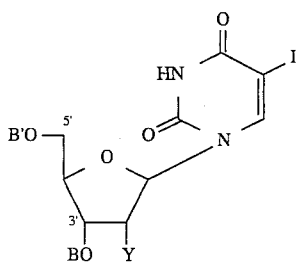

where B and B' are hydroxy protecting groups which may be the same or different, and Y is as previously defined;

with H—C≡C—X'NR, where X' and R are as defined previously, in the presence of (Ph₃P)₂ PdCl₂ and CuI, at room temperature to form:

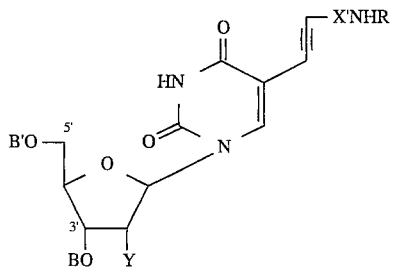

(B) Removing the protecting groups B and B' from compounds of the formula (2) to form:

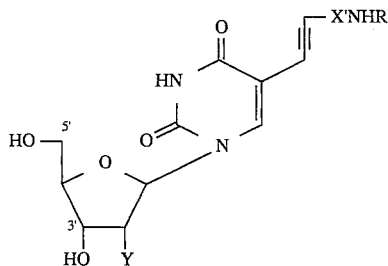

Compounds of formula (3) may be converted into other compounds, in accordance with the invention, by further reactions.

(C) Compound (3) may be reacted with a compound of the formula B"A', where B" is a protecting group such as any derivative of the trityl group, and A' is a leaving group to form:

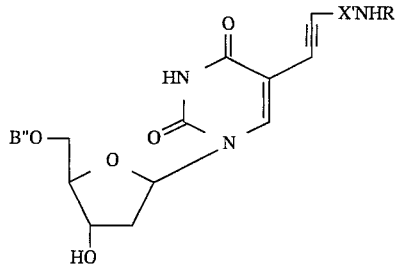

(D) Compound (4) may be reacted with a compound of the formula XR', where R' is a leaving group and X is as previously defined, to form:

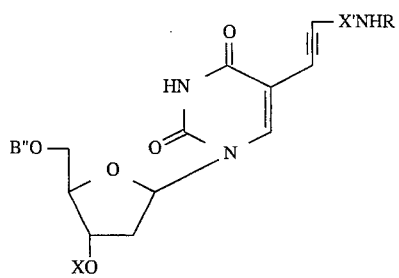

(E) Compound (5) may be reacted with, for example, either an acid or base depending on whether protecting group B" is acid or base labile to effect removal of the group B", and then reacted with POCl₃ in the presence of triethylphosphate to form:

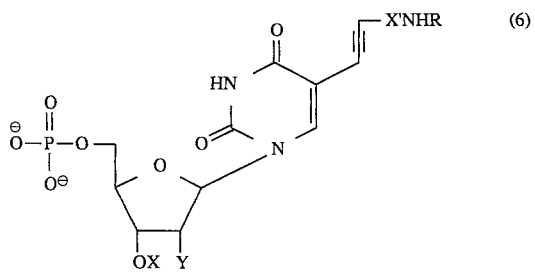

(F) Compound (6) may be reacted first with carbonyldiimidazole and then with tris(tetra-butylammonium)pyrosphate or tributylammonium-pyrophosphate to form:

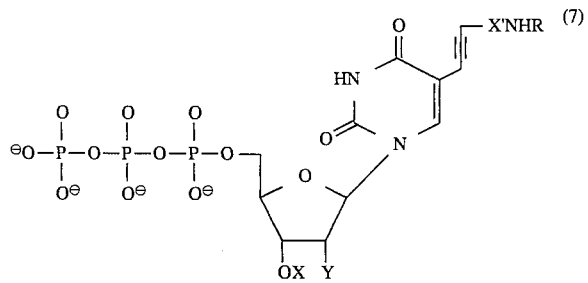

Compound (7) which is one of a preferred class of compounds of the invention may, by virtue of its 5'triphosphate group be purified by ion-exchange chromatography, reverse phase chromatography or cellulose chromatography.

Any conventional leaving group R' may be employed in the above reaction (D). Examples of such groups are Cl, Br, I, p-nitrophenyloxy, pentafluorophenyloxy and diisopropylamino. B" may be the same as B and B' or different. B" may be selectively introduced to the 5'hydroxyl using standard techniques known per se in the art.

The chain length of the C-5 substituent of compounds of the formula (2), where R is an amino protecting group such as BOC, may be extended by treatment with acid to remove the group R, followed by reaction with an active ester of the type

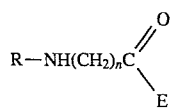

where R is an amino protecting group, n is from 1 to 50 and E is a good leaving group (known per se in the art) such as p-nitrophenyloxy or pentafluorophenyloxy, in the presence of (1,8-diazacyclo[4.4.0]undec-7-ene) DBU to form

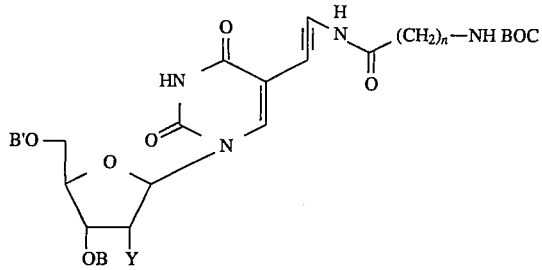

This process may be carried out as many times as desired to increase the chain length of the carbon 5 substituent.

As the skilled person will readily appreciate, in compounds of the formula (I) where the groups R or A are an amino protecting group, such as BOC; the protective group may be removed under appropriate conditions, and a fluorophore or other non-radioactive marker reacted with the free amino group, thereby producing a nucleoside derivative which is labelled with a fluorophore or other non-radioactive marker.

Polynucleotides may be prepared using compounds of the formula (I).

According to another aspect of the invention, there is provided s polynucleotide, characterized in that it contains one or more nucleotide units of the formula (III)

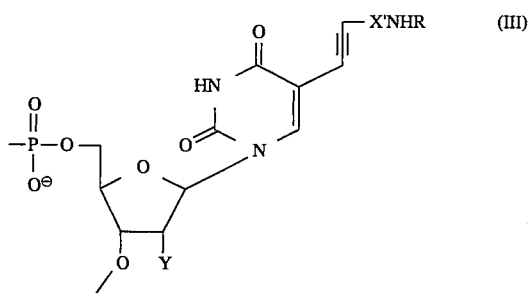

wherein X', Y and R are as previously defined.

The nucleotide unit (III) depicts a compound of the formula (I) incorporated in a polynucleotide chain.

Compounds of the formula (I) may be incorporated into cDNA, synthetic oligonucleotides and RNA using standard procedures[7, 8-12].

According to a further aspect of the invention there is provided a method for the synthesis of a polynucleotide wherein individual nucleotides or groups of nucleotides are sequentially attached to a growing nucleotide chain, characterized in that at least one of the nucleotides is a nucleoside derivative of the formula (I) as previously defined.

More particularly, polynucleotides which contain one or more nucleotide derivatives of the formula (III) may be prepared by reacting together:

(a) a first polynucleotide;
(b) a second polynucleotide which hybridises to a portion of the first polynucleotide;
(c) one or more nucleotide triphosphates;
(d) a DNA polymerase or RNA polymerase;

whereby a polynucleotide is synthesised from the 3' end of said second polynucleotide, characterised in that at least one of said nucleotide triphosphates is a nucleoside derivative of the formula (I) wherein Z is triphosphate and X is hydrogen.

Polynucleotides which contain one or more nucleoside derivatives may also be prepared, in accordance with another aspect of the invention, by sequentially coupling nucleotides together through their respective 5' and 3' ends, characterised in that at least one of said nucleotides is a nucleoside derivative of the formula (I) wherein X is selected from phosphonate or a group of the formula

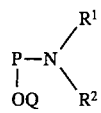

wherein $R^1$, $R^2$ and Q are as previously defined

Compounds of the formula (I) may be incorporated into synthetic oligonucleotides using standard phosphotriester chemistry[19].

For incorporation into RNA, the compounds of the formula (1) have a 5' triphosphate group, and hydroxyl groups at the 3' and 2' positions.

Polynucleotides labelled at multiple sites may be produced according to one aspect of the invention. The effect of multiple labelling is advantageous, as the read-out signal is enhanced over that produced by polynucleotides labelled at a single position.

Where nucleoside derivatives of the formula (I) do not contain a fluorophore or non-radioactive detectable marker prior to incorporation into a polynucleotide, a detectable label may be subsequently introduced into the formed polynucleotide. For example, this may be done by removing a protecting group masking the aliphatic amino group on the C-5 substituent, and then reacting the thus produced amino groups with a fluorophore such as fluoroscein-5-isothiocyanate.

Nucleosides containing non-fluorescent fluorophore analogues (fluorophore precursors) may be used in the preparation of polynucleotides. The use of fluorophore precursors avoid the possibility of fluorophore bleaching during the chemical manipulations necessary for the preparation of polynucleotides. Under appropriate conditions (for example, ammonia treatment) those groups on a fluorophore precursor which suppress fluoresence may be removed thus converting the fluorophore precursor to a flourescent form. By way of example, a reaction scheme for the preparation of a nucleoside derivative of the formula (I) containing a non-fluorescent analogue of fluorescein is shown in FIG. 2. The resultant compound B of FIG. 2 has the following formula:

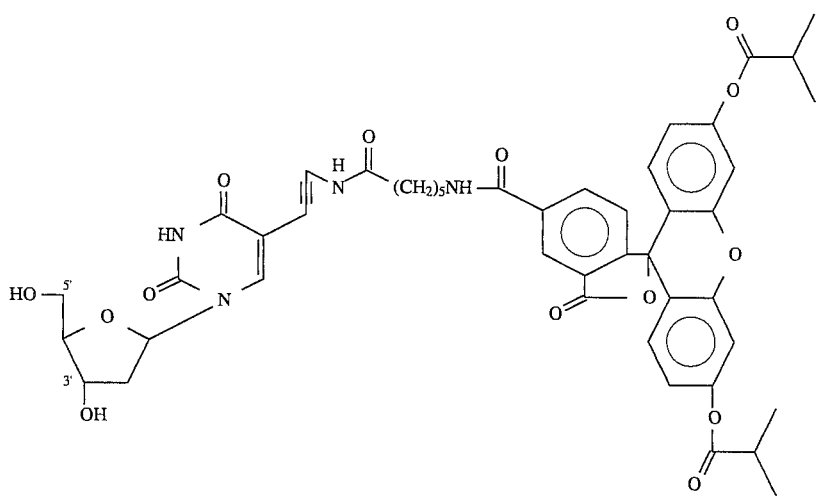

Compound B will fluoresce on removal of the iso-butyryl groups following ammonia treatment.

Compound B may be used in oligonucleotide synthesis (in a protected 5', 3' phosphoramidite form) or cDNA synthesis (in a 5'triphosphate form). A uridine analogue of the compound B may be used in RNA synthesis with T7 polymerase[11] or SP6 polymerase[12].

The compounds of the present invention are useful in molecular biological techniques which normally utilise isotopically labelled probes. Such techniques include DNA and RNA hybridizations such as dot blots, Southern blots, hybridization histochemistry, Northern blots and plaque hybridizations.

The nucleoside derivatives of the formula (I) or polydeoxynucleotides incorporating such nucleoside derivatives may be used in DNA sequencing reactions.

According to another aspect of the invention, there is provided a method of sequencing DNA which comprises the steps of:

(a) providing a first reaction mixture comprising:
(i) a polydeoxynucleotide;
(ii) a polydeoxynucleotide primer capable of hybridizing to part of the polydeoxynucleotide (i);
(iii) dATP, dGTP, dCTP, dTTP;
(iv) ddATP;
(v) a DNA polymerase or the Klenow fragment of DNA polymerase;

(b) providing a second reaction mixture which is the same as said first reaction mixture, except that the ddATP is replaced with ddGTP;

(c) providing a third reaction mixture which is the same as the said first reaction mixture except that ddATP is replaced with ddCTP;

(d) providing a fourth reaction mixture which is the same as the said first reaction mixture except that the ddATP is replaced with ddTTP;

(e) separately incubating the said reaction mixtures to extend in each case the polydeoxynucleotide primer from its 3' end to produce polydeoxynucleotides of different lengths, the number of nucleotides in each thereby newly synthesised polynucleotide being determined by the incorporation of a dideoxynucleotide into the growing chain;

(f) fractionating reaction mixtures (a) to (d) by passage through a gel matrix;

characterized in that the polydeoxynucleotide primer (ii) is a polydeoxynucleotide containing one or more nucleotide units of the formula (III) as previously described wherein R and A is a fluorophore, or other non-radioactive detectable marker, and/or each said reaction mixture contains a nucleoside derivative of the formula (I), wherein Z is triphosphate, X is hydrogen, and R or A is a fluorophore, or other detectable marker; whereby the fluorophore, or other non-radioactive detectable marker, is incorporated into each newly synthesized polydeoxynucleotide;

and that the relative positions of the newly synthesized polydeoxynucleotides separated on the gel matrix are identified by detection of the fluorophore, or other non-radioactive detectable marker, carried by the newly synthesized polydeoxynucleotide, thus allowing the DNA sequence of the first polynucleotide to be elucidated.

The newly synthesized polynucleotides of step (e) above may, for example, be detected by fluoresence induced by irradiation with a light source, such as a laser.

Each of reaction mixtures (a) to (d) above may contain a different fluorophore having different emission maxima, or a different non-radioactive detectable marker. That is, the oligonucleotide primer (ii) and/or the nucleoside derivative of the formula (I) in each of reaction mixtures (a) to (d) contains groups R or A having a distinct emission maxima.

BRIEF DESCRIPTION OF THE DRAWINGS

Several embodiments of the present invention will now be described, by way of example only, with reference to the accompanying figures in which:

FIG. 6 shows dot blot hybridization assays with the short C-5 arm fluorescently labelled kallikrein oligonucleotides to mouse salivary gland mRNA. The probes were $^{32}$P end-labelled and hybridized as explained hereinafter;

FIG. 7 shows dot blot hybridization assays with the long C-5 arm fluorescently labelled kallikrein probe. The probes were $^{32}$P end-labelled and hybridized under conditions of high stringency. Exposure times for the autoradiographs were 4 hr;

FIG. 8 shows dot blot hybridization assays with the $^{32}$P end-labelled, singly fluorescent labelled kallikrein probes to three different RNA species. Hybridizations were carried out under conditions of intermediate stringency and exposure time for the autoradiographs was 16 hr;

MATERIALS AND METHODS

Figure 1:
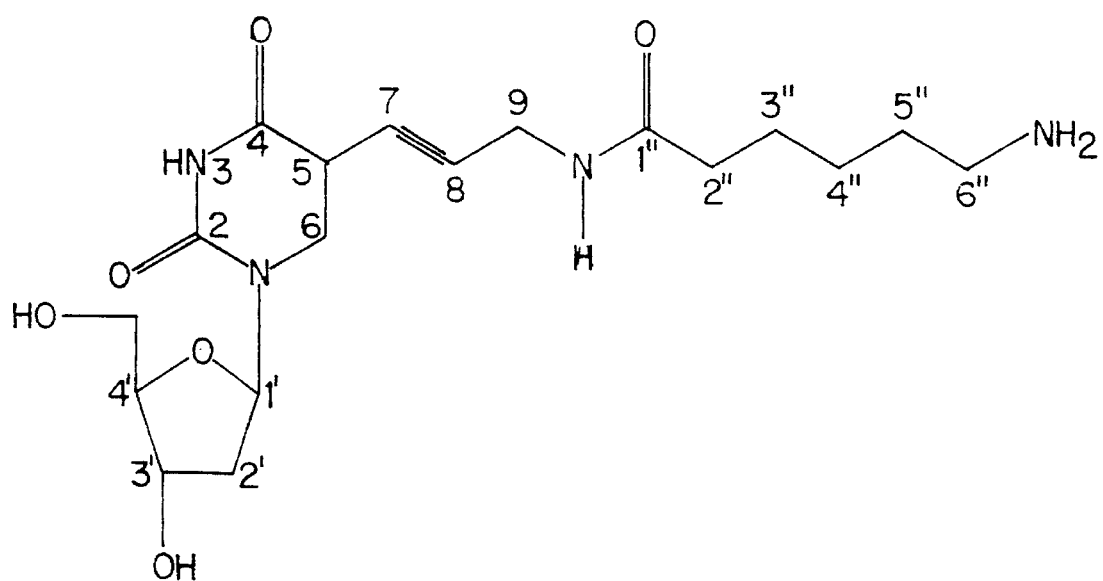
FIG. 1 shows the numbering system for C-5 substituted nucleosides, used in this specification.

5-Iododeoxyaridine and fluorescein isothiocyanate (FITC) were obtained from Sigma Chemical Company. $^1$H NMR spectra were run on either of JEOL FX90Q at 90 MHz, a JEOL FX100 at 100 MHz, or a BRUKER 300 at 300 MHz. $^{13}$C NMR spectra were run on either a JEOL FX90Q operating at 22.5 MHz, a JEOL FX100 at 25 MHz, or a BRUKER 300 at 75 MHz. Multiplicities, where observed, were measured by the single frequency off resonance (SFOR) method in the case of the JEOL FX90Q or FX100, and on the BRUKER 300 by using the DEPT pulse sequence. The nucleoside numbering system used in the NMR analysis is shown in the case of the parent nucleoside in FIG. 1. $^{31}$P NMR spectra were obtained with a BRUKER 300, operating at 121 MHz, and measuring downfield from 85% $H_3PO_4$ as external reference, downfield values being positive. Microanalyses were determined by the Australian Microanalytical Service, Melbourne. Pyridine was distilled from potassium hydroxide, and stored over 5A molecular sieves. Acetonitrile and methanol were dried over 3A molecular sieves. Triethylamine was distilled from calcium hydride and stored under argon. Dichloromethane used in phosphoramidite syntheses was dried over 5A molecular sieves. Tetrazole was sublimed at 0.05 mmHg at 110° C. Diisopropylamine was distilled from calcium hydride and stored over 3A molecular sieves. Thin layer chromatography (tlc) was carried out on Merck analytical silica gel plates (Merck No. 5735) using the following solvent systems: S1, $CH_2Cl_2$/MeOH (90:10 v/v), S2, $CH_2Cl_2$/MeOH (98:2 v/v) or S3, $CH_2Cl_2$/EtOAc/$Et_3N$ (45:45:10 v/v). Melting points were determined in open ended capillaries on an Electrothermal Melting Point Apparatus.

EXAMPLE 1: Synthesis of Nucleoside Analogues

3',5'-Di-O-p-toluoyl-5-iododeoxyuridine (1)

The title compound was prepared by a modification of the method of Robins et al.[18] using 5-iododeoxyuridine instead of deoxTuridine, in 92% yield; mp 205°–206° C. (lit[14] 195–196). $^{13}$C NMR (CDCl$_3$, 25 MHz) δ 21.7 (CH$_3$), 38.7 (C-2'), 64.1 (C-5'), 69.0 (C-5), 74.9 (C-3'), 83.4 (C-1'), 85.8 (C-4'), 126.1, 126.4 (tol C-1), 129.3, 129.5; 129.8 (tol C-2, C-3, C-5 and C-6), 143.6 (C-6), 144.6 (tol C-4) 149.2 (C-2), 159.7 (C-4), 166.0 (tol C-0).

3-tert-Butyloxycarbonylamidopropyne:

To 200 mL of $CH_2Cl_2$ was added 2.75 g (50 mmol) of 3-aminopropyne, followed by 10.92 g (50 mmol) of di-tert-butylpyrocarbonate. After stirring for 3 h, the reaction mixture was evaporated to a syrup, and kept at −20° C. to crystallize. The product was filtered off, washed with hexane and dried to give 5.34 g (69%), mp 42°–44° C. (lit[13] mp 43° C.). $^1$H NMR (CDCl$_3$, 90 MHz) δ 1.46 (9H, s, CH$_3$), 2.21 (1H, t, J-2.6 Hz, C≡CH), 3.91 (2H, dd, J=2.6 Hz and 3.5 Hz, CH$_2$) 4.68 (1H, br s, NH). $^{13}$C NMR (CDCl$_3$, 22.5 MHz) δ 28.4 (CH$_3$), 30.6 (CH$_2$), 71.2 (C-1), 80.1 ($\underline{C}$(CH$_3$)$_3$), 80.2 (C-2), 155.3 (C=0).

5-(3-tert-Butyloxycarbonylamidoprop-1-ynyl)-3',5'-di-O-p-toluoyldeoxyuridine (2)

To 500 mL of deoxygenated ethyl acetate was added 5.90 g (10 mmol) of 3',5'-di-O-p-toluoyl-5-iododeoxyuridine (1), followed by 3.10 g (20 mmol) of N-BOC-3-aminopropyne, 150 mg of (Ph$_3$P)$_2$PdCl$_2$, 150 mg of CuI and 6.7 mL of triethylamine (50 mmol). The resulting suspension was stirred at room temperature, and the reaction followed by tlc (S2).

After 90 h, the starting material had disappeared. A further 200 mL of ethyl acetate was then added, and the resulting solution was washed with 5% disodium EDTA/$H_2O$ (2×300 mL), $H_2O$ (300 mL) and brine (300 mL). It was then dried (Na$_2$SO$_4$), the solvent evaporated, and the residue redissolved in 15 mL of solvent S3 and purified by flash chromatography[13] using the same solvent, yield 5.08 g (84%). A sample was recrystallized from CHCl$_3$/MeOH 1:5 to give 2: mp 169.5°–170.5° C. UV(MeOH) λ$_{max}$ 290(sh), 283,237 nm (ε 11800, 12400, 39800), λ$_{min}$ 263 nm (ε 5900). $^1$H NMR (CDCl$_3$, 90 MHz) δ 1.44 (9H, s, C(CH$_3$)$_3$), 2.42 (6H, s, tol CH$_3$), 2.7 (2H, m, H$_2$'), 3.97 (2H, d, J=5.1 Hz, Hg), 4.6–4.7 (4H, m, H$_4$', H$_5$' and BOC NH), 5.6 (1H, m, H$_3$'), 6.4 (1H, m, H$_1$'), 7.26 (4H, d, J=8.1 Hz, tol H$_3$ and H$_6$), 9.16 (1H, m, H$_3$'), 6.4 (1H, m, H$_1$'), 7.26 (4H, d, J=8.1 Hz, tol H$_3$ and H$_6$), 9.16 (1H, s, ring NH). $^{13}$C NMR (CDCl$_3$, 22.5 MHz) δ 21.7 (q, tol CH$_3$), 28.4 (q, C($\underline{C}$H$_3$)$_3$), 31.4 (t, C-9), 38.6 (t, C-2'), 64.1 (t, C-5'), 73.8 (s, C-8), 74.9 (d, C-3'), 80.0 (s, $\underline{C}$(CH$_3$)$_3$, 83.4 (d, C-1'), 86.1 (d, C-4'), 90.3 (s, C_7), 100.2 (s, C-5), 126.4 and 126.6 (2s, tol C-1), 129.3–129.9 (4s, tol C-2, C-3, C-5 and C-6), 141.9 (d, C-6), 144.5 (s, tol C-4), 149.2 (s, C-2), 155.3 (s, BOC C=0), 161.7 (s, C-4), 166.04 and 166.15 (2s tol C=0). Anal. Calcd for C$_{33}$H$_{35}$O$_9$N$_3$: C, 64.17; H, 5.71; N, 6.80. Found: C, 63.94: H, 5.52; N, 6.55.

5-(3-tert-Butyloxycarbonylamidoprop-1-ynyl)-5'-O-dimethoxytrityldeoxyuridine (5)

To a stirred suspension of 304 mg (2.2 mmol) of dry $K_2CO_3$ in 5 mL of dry methanol was added 617 mg (1 mmol) of 2. After 1.5 h the reaction mixture then filtered, and the filtrate neutralized with Dowex 50-X8(H$^+$), the resin filtered off, and the filtrate evaporated to dryness to give 4. The product was thoroughly dried by coevaporation with dry pyridine (3×5 mL) and redissolved in 5 mL of dry pyridine. 406 mg (1.2 mmol) of 4,4'-dimethoxytrityl chloride was added, and the mixture was stirred for 4 h at room temperature, after which time the reaction was judged complete by tlc (S1). 2 mL of MeOH was added, the solution was stirred for a further 10 min, evaporated, redissolved in 30 mL of dichloromethane, washed with 10% NaHCO$_3$/H$_2$O (30 mL), brine (30 mL), and dried (Na$_2$SO$_4$). The solvent was again evaporated and the product redissolved in 5 mL of CH$_2$Cl$_2$ and purified by flash chromatography, eluting first with 300 mL of 2% MeOH/CH$_2$Cl$_2$ and then with 10% MeOH, CH$_2$Cl$_2$. The fractions containing the product were pooled and evaporated to dryness to give 468 mg (68% from 2) of 5. UV(MeOH) $\lambda_{max}$ 294(sh), 283, 231 nm ($\epsilon$ 6100, 6800, 21500), $\lambda_{min}$ 257 nm (2500). $^1$H NMR (CDCl$_3$, 100 MHz) $\delta$ 1.39 (9H, s, BOC CH$_3$), 2.4 (2H, m, H$_2$'), 338 (2H, m, H$_5$'), 3.78 (8H, s), OCH$_3$ plus H$_9$), 4.1 (1H, m, H$_4$'), 4.6 (3H, m, H$_3$'+BOC NH), 6.32 (1H, t, H$_1$'), 6.80, 6.89 (4H, d, J=9.0 Hz, mete CH of PhOCH$_3$), 7.2–7.5 (9H, m, including a doublet at 7.29, 7.34 (J=9.0 Hz) of ortho cH of PhOCH$_3$, and Ph), 8.11 (1H, s, H6). Anal. Calcd for C$_{38}$H$_{41}$O$_9$N$_3$: C, 66.75; H, 6.04; N, 6.15. Found: C, 66.89; H, 5.82; N, 6.00.

The nucleoside 4 was also purified by flash chromatography (20% MeOH/CH$_2$Cl$_2$ as eluant) of the crude reaction mixture from the deprotection reaction, after filtration of the potassium carbonate. This gave 4, $^1$H NMR (d$_6$-DMSO, 100 MHz) $\delta$ 1.39 (9H, s, CH$_3$), 2.1 (2H, m, H$_2$'), 3.35 (6H, s, 2 molecules of methanol present in the sample), 3.6 (2H, m, H$_5$'), 3.8 (1H, m, H$_4$'), 3.93 (2H, d, J=5.9 Hz, H$_9$), 4.2 (1H, m, H$_3$'), 5.10 (1H, t, J=5 Hz, 5'—OH), 2.25 (1H, d, J=4 Hz, 3'—OH), 6.11 (1H, t, J=6.6 Hz, H$_1$'), 8.14 (1H, s, ring NH); UV (MeOH) $\lambda_{max}$ 290, 231 nm ($\epsilon$ 12900, 18200), $\lambda_{min}$ 254 nm ($\epsilon$ 4200), at 260 nm, $\epsilon$=5800 M$^{-1}$.

5-(3-tert-Butyloxycarbonylamidoprop-1-ynyl)-5'-O-di-methoxytrityl-3'-N,N-diisopropylaminomethoxyphosphinyl-deoxyuridine (7)

To an argon flushed 25 mL round bottomed flask was added a solution of 243 mg (0.5 mmol) of 5, in 5 mL of dry CH$_2$Cl$_2$. This was followed by 17.5 mg (0.25 mmol) of tetrazole and 25 μL (0.25 mmole) of dry diisopropylamine. The solution was stirred until the tetrazole dissolved. 300 μL (1.1 mmol) of bis(diisopropylamino)methoxyphosphine[17] 6 was then added, and the reaction followed by tlc (S3). After 5 h, the reaction mixture was washed with 10% NaHCO$_3$/H$_2$O (2×25 mL), brine (2×25 mL), and dried (Na$_2$SO$_4$). The solvent was evaporated to give 392 mg (93% crude yield) of 7. The $^{31}$P NMR spectrum of this material showed a major peak comprised of a doublet at 150.19 and 150.45 ppm and minor peaks at 4.23 and 10.41 ppm. These by-products do not interfere with the coupling reaction.

Some of this material was purified by flash chromatography (S3). $^1$H NMR (CD$_3$CN, 100 MHz) $\delta$ 1.13 (12 H, 2d, J=6.5 Hz, CH(CH$_3$)$_2$), 1.38 (9H, s, BOC CH$_3$), 2.4 (2H, m, H$_2$'), 3.2–3.5 (5H, m containing 2d (J=13.3 Hz, PCH$_3$) and H$_5$'), 3.5 (2H, m, CH(CH$_3$)$_2$), 3.7–3.8 (8H, m containing one strong singlet at 3.77 (trityl OCH$_3$) and H$_9$), 4.1 (1H, m, H$_4$'), 4.6 (1H, m, H$_3$'), 6.1 (1H, dt, H$_1$'), 6–8-7.5 (13H, m, trityl CH), 7.90 and 7.91 (1H, 2s, H$_6$).

5-(3-Aminoprop-1-ynyl)-3'5'-di-O-p-toluoyldeoxyuridine, trifluoroacetate salt (8)

To 20 mL of 95% CF$_3$CO$_2$H/H$_2$O (TFA/H$_2$O) was added 3.09 g (5 mmol) of 2. After being stirred for 10 min, the solvent was evaporated to dryness. 10 mL of ethyl acetate was then added, it was evaporated again, the product crystallized and was filtered and dried to give 2.56 g (81%) of 8, mp 120° C. (dec). UV(MeOH) $\lambda_{max}$ 290(sh), 282, 236 nm ($\epsilon$ 11900, 12400, 41200), $\lambda_{min}$ 263 nm ($\epsilon$ 9000). $^1$H NMR (90 MHz, d$_6$-DMSO) $\delta$ 2.39 (6H, s, CH$_3$, 2.5–2.6 (m, solvent plus H$_2$'), 3.7 (m, H$_2$O impurity in solvent plus H$_9$), 4.6 (3H, m, H$_4$' and H$_5$'), 5.6 (1H, m, H$_3$'), 6.24 (1H, t, H$_1$'), 7.34 (4H, 2d, J=8.1 Hz, tol H$_2$ and H$_6$), 7.90 (4H, 2d, J=8.1 Hz, tol H$_3$ and H$_5$), 8.07 (1H, s, H$_6$), 8.3 (3H, bs, NH$_3$ $^+$), 11.80 (1H, s, ring NH). $^{13}$C NMR (75 MHz, d$_6$-DMSO) $\delta$ 21.2 (CH$_3$), 29.0 (C-9), 36.4 (C-2'), 64.2 (C-5'), 74.4 (C-3'), 78.5 (C-8), 81.5 (C-1'), 85.2 (C-7), 85.7 (C-4'), 97.6 (C-5), 126.4 (tol C-1), 129.3, 129.5 (tol C-2,C-3, C-5 and C-6), 143.9 (C-6), 144.8 (tol C-4), 149.3 (C-2), 161.3 (C-4), 165.2 (carboxyl), 165.6 (tol C=0). Anal. Calcd for C$_{30}$H$_{28}$O$_9$N$_3$F$_3$: C, 57.05; H, 4.47; N, 6.65; F, 902. Found: C, 57.12; H, 4.75; N, 6.42; F, 9.1.

6-tert-Butyloxycarbonylamidohexanoic acid

To 13.12 g (100 mmol) of 6-aminohexanoic acid in 400 mL of dioxan at 0° C. was added 100 mL of 1M NaOH, and 24.01 g (110 mmol) of di-tert-butyl-pyrocarbonate. The resulting suspension was stirred at room temperature for 3 days, after which time it gave a negative ninhydrin test. The volume was then reduced under pressure to 100 mL, the mixture cooled to 0° C., covered with ethyl acetate, and acidified with 1M KHSO$_4$ to pH 2–3. The product was extracted with ethyl acetate (3×150 mL), the organic phase washed with H$_2$O (2×300 mL), dried (Na$_2$SO$_4$) and evaporated to a thick syrup. This was recrystallized from ethyl acetate/hexane, to give 20.40 g (88%), mp 39°–41° C. (lit[14] mp 39.5° C.).

p-Nitrophenyl 6-tert-butyloxycarbonylamidohexanoate (9)

To a solution of 2.31 g (10 mmol) of 6-tert-butyloxycarbonylamidohexanoic acid and 1.62 g (12 mmol) of p-nitrophenol in 30 mL of EtOAc at 0° C. was added dropwise 2.06 g (10 mmol) of dicyclohexycarbodiimide. This solution was stirred at 0° C. for 0.5 h, and then at room temperature for 3.5 h, filtered to remove the dicyclohexylurea, evaporated to dryness and the product recrystallized from 95% EtOH containing 1% acetic acid, to give 3.35 g (95%) of 9, mp 119°–120° C. (lit[14] mp 116.5° C.).

5-[N-(6-tert-Butyloxycarbonylamidohexanoyl)-3-amino-prop-1-ynyl)]-3',5'-di-O-p-toluoyldeoxyuridine (10)

To a solution of 1.89 g (3 mmol) of 8 in 30 mL of dry DMF was added 443 μL of DBU (3 mmol) and 1.16 g (3.3 mmol) of 9. After being stirred for 1 h, the mixture was evaporated under vacuum, the residue redissolved in 50 mL of CH$_2$Cl$_2$ and 400 mL of ethyl acetate, washed with H$_2$O (2×300 mL), brine (300 mL), dried (Na$_2$SO$_4$), and evaporated to dryness. The solid was recrystallized from methanol to give 1.76 g (80%) of 10, mp 192°–194° C. UV(MeOH) $\lambda_{max}$ 290 (sh), 282, 237 nm ($\epsilon$ 13800, 14400, 43000), $\lambda_{min}$ 262 nm ($\epsilon$ 10300). $^1$H NMR (CDCl$_3$, 100 MHz) $\delta$ 1.4–1.9 (15H, m with s at 1.43 (BOC CH$_3$) and H$_3$", H$_4$" and H$_5$"), 2.16 (2H, 5, J=7.5 Hz, H$_2$"), 2.42 (6H, s, tol CH$_3$), 2.75 (2H, m, H$_2$'), 3.1 (2H, m, H$_6$"), 4.04 (2H, d, J=5.0 Hz, H$_9$), 4.5–4.8 (4H, m, H$_4$', H$_5$' and BOC NH), 5.6 (1H, m, H$_3$'), 6.31 (1H, dd, H$_1$'), 7.27 (4H, d, J=8.2 Hz, tol H$_3$ and H$_5$), 7.84 (1H, s, H$_6$), 7.91 and 7.93 (4H, 2d, J=8.2 Hz, tol H$_1$ and $H_6$), 9.0 (1H, br s, ring NH). $^{13}$C NMR (CDCl$_3$, 75 MHz) δ 21.7 (tol CH$_3$), 25.2 (C-4"), 26.4 (C-3"), 28.4 (BOC CH$_3$), 29.7 (C-5"), 30.0 (C-9), 36.1 (C-2"), 38.6 (C-2'), 40.4 (C-6"), 64.2 (C-5'), 74.0 (C-8), 74.8 (C-3'), 79.8 ( $\underline{C}$(CH$_3$)$_3$), 83.4 (C-1'), 86.0 (C-4'), 89.9 (C-7), 100.0 (C-5), 126.2, 126.4 (tol C-1), 129.3, 129.5, 129.6 and 129.8 (tol CH), 142.1 (C-6), 144.8 (tol C-4), 149.1 (C-2), 156.1 (BOC C=O), 161.9 (C-4), 166.0, 166.2 (tol C=O), 172.3 (C-1"). Anal. Calcd for C$_{39}$H$_{46}$O$_{10}$N$_4$: C, 64.10; H, 6.34; N, 7.67. Found: C, 64.34; H, 6.32; N, 7.51.

5-[N-(6-tert-Butyloxycarbonylamidohexanoyl)-3-amino-prop-1-ynyl)]-5'-O-dimethoxytrityldeoxyuridine (12)

The title compound was prepared from 10 using the same method as that used to prepare 5 from 2. Yield 1.20 g (75% from 10). UV(MeOH) $\lambda_{max}$ 293(sh) 283, 233 nm (ε 8500, 9000, 24500), $\lambda_{min}$ 257 nm (ε 2900). The $^1$H NMR spectrum of this compound was a composite of those resonances arising from the deoxyribose part of 5 and those from the heterocyclic base part of 10. $^{13}$C NMR (CDCl$_3$, 75 MHz) δ 25.1 (C-4"), 26.4 (C-3"), 28.4 (C(CH$_3$)$_3$, 29.7 (C-5"), 30.0 (C-9), 35.9 (C-2"), 40.4 (C-6"), 41.7 (C-2'), 55.3 (OCH$_3$), 63.6 (C-5'), 72.2 (C-3'), 74.1 (C-8), 79.2 (C(CH$_3$)$_3$), 86.0 (C-4'), 86.8 (C-1'), 87.0 (trityl central C), 89.7 (C-7), 99.5 (C-5), 113.4 (methoxyphenyl C-3 and C-5), 127.0, 127.9 and 128.1 (phenyl CH), 130.0 (methoxyphenyl C-2 and C-6), 135.6 (methoxyphenyl C-1), 143.1 (C-6), 144.6 (phenyl C-1), 149.4 (C-2), 156.0 (BOC C=O), 158.6 (methoxyphenyl C-4), 162.5 (C-4), 172.7 (C-1"). Anal. Calcd for C$_{44}$H$_{52}$O$_{10}$M$_4$: C, 66.32; H, 6.58; N, 702. Found: C, 65.94; H, 6.52; N. 6.70.

5-[N-(6-tert-Butyloxycarbonylamidohexanoyl)-3-amino-prop-1-ynyl)]-5'-O-dimethoxytrityl-3'-N,N-di-isopropyl-aminomethoxyphosphinyldeoxyuridine (11)

The preparation of 11 was similar to that of 7, except that the reaction was allowed to proceed for 4 h, and a further 30 mL of CH$_2$Cl$_2$ was added to the reaction mixture before the washes. The washed and dried solution was evaporated to dryness under vacuum, to give 903 mg (94% crude yield) of 11. $^{31}$P NMR of this material showed a major peak at 149.86 ppm, with minor peaks at 7.35, 13.06 and 18.25 ppm.

EXAMPLE 2

Coupling of phosphoramidites 7 and 11 to the 5'-hydroxyl of an oligonucleotide The methods used to add the modified nucleoside phosphoramidites to the 5'-end of a fully protected, solid support bound oligonucleotide were standard[20]. The fully protected resin-bound oligonucleotide was synthesized on the Applied Biosystems 380A DNA Synthesizer, on a 1 μmole scale. The solid support was then transferred to a manual reaction cell. This cell was similar to a miniature chromatography column, 1 cm in diameter and 3 cm long, with a B14 quick-fit top and a medium porosity sintered glass disc with a 3-way teflon tap at the bottom. Following detritylation (3% dichloroacetic acid/CH$_2$Cl$_2$), the resin was washed thoroughly with dry CH$_3$CN, and left under argon. 10 μmole of the phosphoramidite and 40 μmole of tetrazole were then added, followed by 1 ml of dry CH$_3$CN. The cell was shaken for 15 min, drained, and the phosphite triesters oxidized with 0.1M iodine solution in the usual way. A trityl assay was carried out on a small sample to quantify the extent of reaction. Following removal of the methyl protecting groups on phosphate (thiophenoxide ion, 2 h), the resin was treated with 90% TFA/ethanedithiol for 5 min, drained, washed thoroughly with CH$_3$CN, with a total of 20 mL at 20% Et$_3$N/CH$_2$Cl$_2$, and then again with CH$_3$CN and dried. The oligonucleotide was then cleaved from the support with 35% aqueous NH$_3$ (4 mL), and the resulting solution kept at 55° C. overnight to remove the base protecting groups. Evaporation to dryness gave the product which was redissolved in H$_2$O (3 mL).

The oligonucleotides were purified by polyacrylamide gel electrophoresis. The product was the slowest moving major band, running at ~1–2 nucleotides slower than the underivatized oligonucleotide. Typically, ~150 μL of the oligonucleotide solution was purified on a 10%, 1.5 mm thick, 20 cm long polyacrylamide gel (25 μL+5 μL formamide per 1 cm×1 cm well). The bands were visualized by UV shadowing, using a fluorescent tlc silica gel sheet as background. The product bands were cut out, eluted in H$_2$O, dialysed, lyophilized, and redissolved in 150 μL of H$_2$O.

EXAMPLE 3

Preparation of oligonucleotides containing internal modified nucleotides

The nucleotide phosphoramidites 7 and 11 were used on the Applied Biosystems DNA synthesizer to prepare oligonucleotides that had their thymidine residues replaced by one or the other of the modified nucleosides. The phosphoramidites were made to either 0.1M (for 7) or 0.15M (for 11) in dry acetonitrile. The syntheses were carried out on a 0.2 μmole scale. The repetitive coupling yields were 99–100%. Following chain assembly, the solid support was transferred to a manual reaction cell and then deprotected and cleaved from the solid support as in the case of the oligonucleotides containing the single 5' modified nucleoside. The final product was redissolved in 2 mL of H$_2$O.

EXAMPLE 4

Dye conjugation to the amino oligonucleotide

The following procedure was used for the conjugation of FITC to the purified oligonucleotide containing a single modified nucleoside at the 5' end. To a solution of 2 mg (5 μmol) of FITC in 20 μL of DMF was added 180 μL of 0.1M K$_2$HPO$_4$, pH 9.0, mixed, and then 100 μL (~30 nmol) of the amino oligonucleotide solution. The mixture was kept in the dark overnight, and then applied to a 10 mL column of Sephadex G-25 (medium) in 0.1M ammonium acetate, pH 9.0. 0.5 mL fractions were collected, and the fluorescent material (detected by illuminating with a UV lamp) eluting in the excluded volume was collected. This was freeze dried, redissolved in 200 μL of 0.1M ammonium acetate, pH 9.0 buffer, and reapplied to another, similar column of Sephadex G-25. The fluorescent fractions were collected as before, pooled and the absorbances at 260 and 495 nm read. From this ratio, the number of fluorescein residues per oligonucleotide molecule was determined using $\epsilon_{260}$ for the modified KPIB and HCAL (see results section for the nucleotide sequences of these oligonucleotides) of 3.2×10$^5$ and 4.4× 10M$^{-1}$ respectively, and $\epsilon_{495}$ for fluorescein of 7×10$^4$M$^{-1}$. The product was then lyophilized, and relyophilized twice from H$_2$O.

For the conjugation of FITC to oligonucleotide with multiple internal amino groups a much larger excess of FITC was used. To a solution of 26 mg (63 μmole) of FITC in 100 μL of DMF was added 100 μL of 1.0M $K_2HPO_4$ pH 9.0, mixed, and then 100 μL (~10 nmol) of the amino oligonucleotide. This was left to react overnight in the dark. It was purified as in the previous case, and the fluorescein loading determined, using $\epsilon_{260}$ for the modified KPIB and HCAL of $3.1\times10^5$ and $4.3\times10^5 M^{-1}$ respectively, and taking into account the absorbance of fluorescein at 260 nm, using $\epsilon_{260}$ for fluorescein of $2\times10^4 M^{-1}$.

EXAMPLE 5

Hybridization with FITC-labelled oligonucleotides

RNA dot blots with polyadenylated RNA derived from mouse salivary glands were prepared as previously described[15]. The amount of RNA decreased by a factor of 3 on each successive dot, starting from an initial value of 1 μg. The nitrocellulose filters were prehybridized for 4 h at 42° C. in a solution of 5×SSC (0.75M NaCl, 0.075M sodium citrate), 50 mM sodium phosphate, pH 6.5, 0.02% bovine serum albumin, Fraction V, 0.02% Ficoll, 0.02% polyvinylpyrrolidone, 30 μg/ml denatured calf thumus DNA, 50% formamide. Hybridizations were performed under four different sets of conditions: high stringency, hybridization at 40° C. for 24 h, and washing with 2×SSC at room temperature; intermediate stringency, as above but hybridizing at room temperature; low stringency, as above but hybridization mixture containing 10% formamide instead of 50%; and lowest stringency, prehybridizing at 4° C., hybridizing at 4° C. with no formamide present, for 5 days, and washing at room temperature with 2×SSC.

RESULTS

Preparation of C-5 substituted nucleotides

Figure 2:
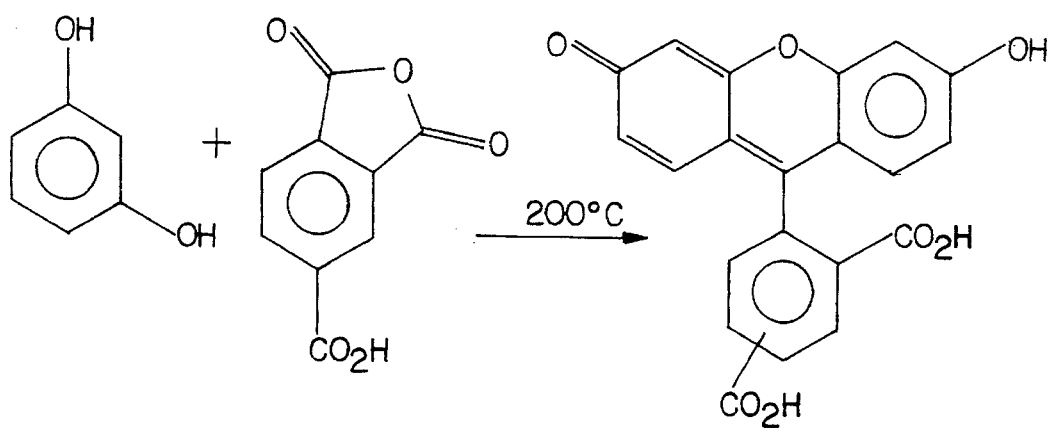
FIG. 2 shows the preparation of nucleoside derivatives of the present invention incorporating a modified nonfluorescent fluoroscein moiety.
Figure 2:
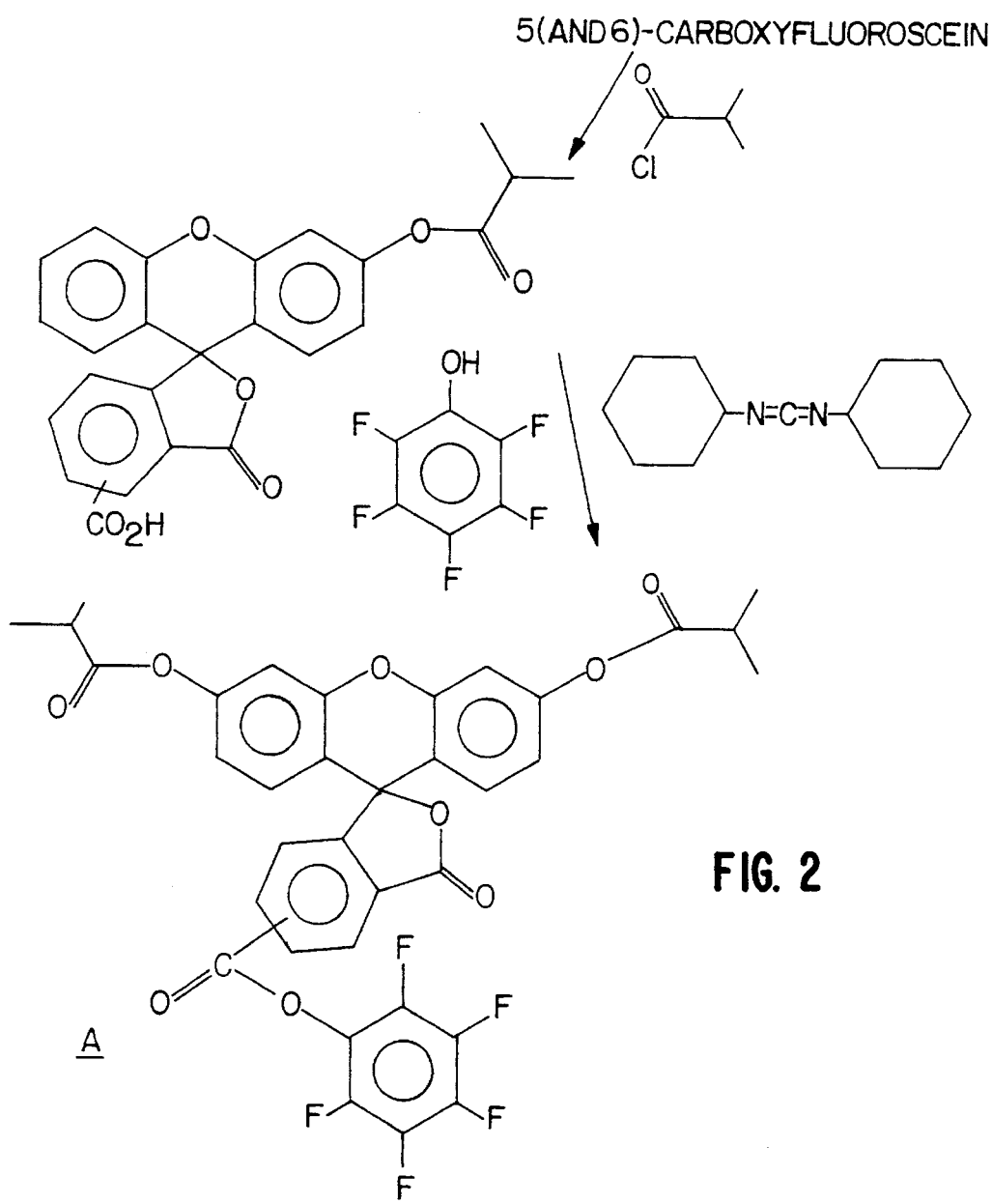
Figure 2A:
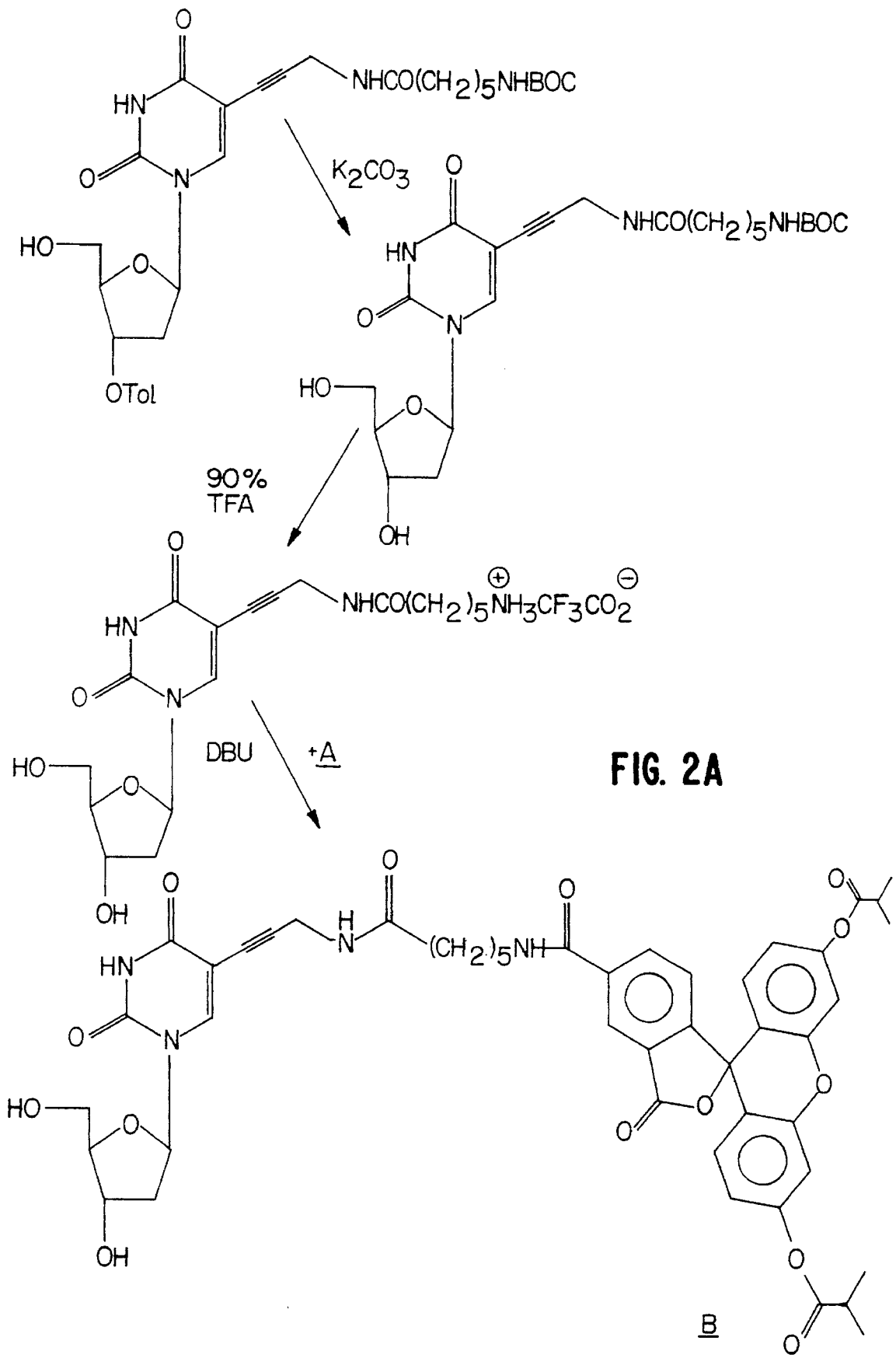
FIG. 2A shows a reaction scheme for the preparation of nucleoside derivatives of the formula (I) containing a non-fluorescent analogue of fluorescein.

The approach used for the preparation of the substituted deoxyuridines is shown in FIG. 2. 3',5'-di-O-p-toluoyl-5-iododeoxyuridine (1), prepared from the commercially available 5-iododeoxyuridine, was condensed with N-BOC-3-aminopropyne, in the presence of catalytic amounts of bis(triphenylphosphine)palladium chloride and cuprous iodide. Robins and Bart have reported this coupling of terminal alkynes with 5-iodouracils and 5-iododeoxyuridines, using alkynes with alkyl, either or ester substituents[18]. The reactions were carried out in triethylamine as the solvent, at 50° C. We tried a variety of conditions to maximise the yield of the product2, and minimize the yield of the major by-product, a fluorescent nucleoside which, by analogy with the work of Robins and Bart, probably has the struction 3. The conditions that we found to give the best yield of 2 were using ethyl acetate as solvent, with a five-fold molar excess of triethylamine over 1, and carrying out the reaction at room temperature. this gave a yield of 84%. The struction of the product was confirmed by $^1H$ and $^{13}C$ NMR spectroscopy. This product is a key compound, from which a number of other derivatives can be obtained.

Figure 3:
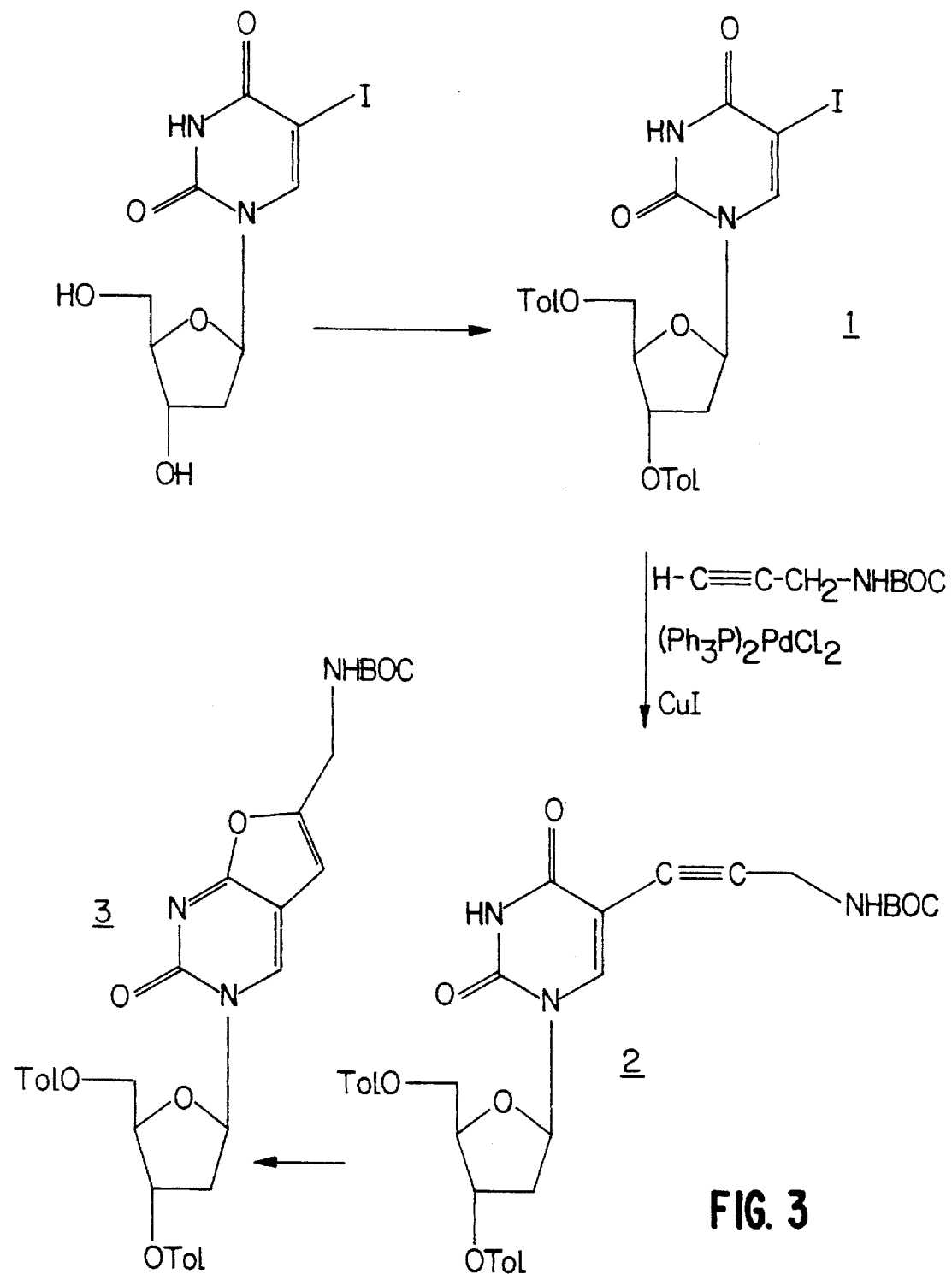
FIG. 3 shows the preparation of the protected aminoalkyne nucleoside 2.

The phosphoramidite 7 was prepared from 3 by a three step procedure, as shown in FIG. 3. The 3',5' ester protecting groups of 2 were removed using potassium carbonate/methanol and the resulting product 4 treated with dimethoxytrityl chloride in pyridine to give 5. The UV spectrum of 4 also provided evidence for the structure of the nucleoside. The absorption maximum of the heterocyclic base shifted from 265 nm in thymidine, to 290 nm in the nucleoside 4, with an accompanying increase in its intensity. This shift in the absorption maximum is seen in all of the derivatives synthesized that contain this chromophore.

Treatment of the 5'-tritylated nucleoside 5 with a two-fold excess of the bis(dialkylamino)phopshine 6; under catalytic conditions, gave the phosphoramidite 7. This method of phosphoramidite preparation is similar to that reported by Caruthers et al[10] for the preparation of phosphoramidites in situ.

EXAMPLE 6

Preparation of nucleosides with a longer linker arm on C-5

Figure 4:
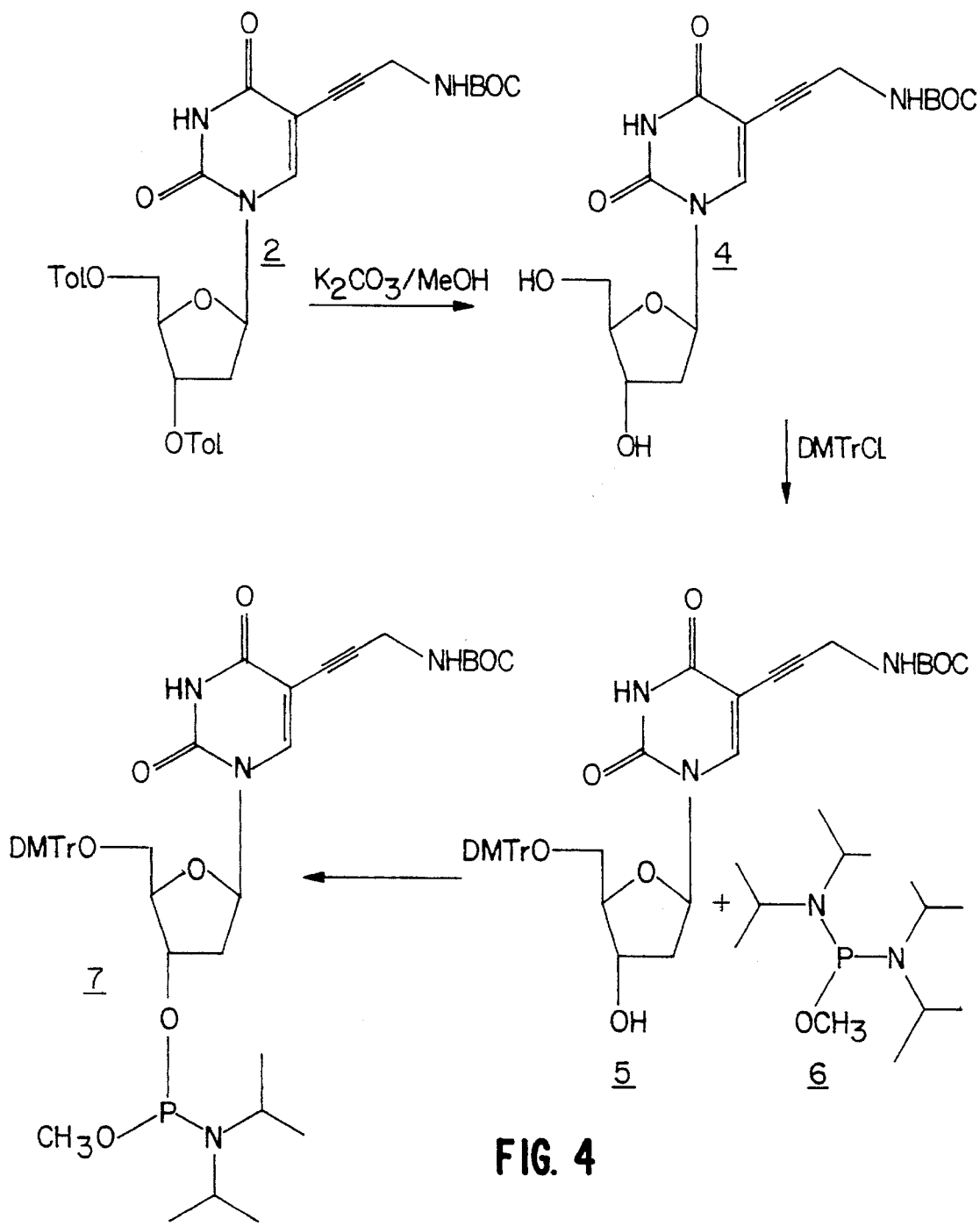
FIG. 4 shows the preparation of the short C-5 arm nucleoside phosphoramidite 7.

Even though 7 can be used to introduce internal primary aliphatic amino groups in an oligonucleotide, as will be described later in this report, it was surmised from the outset that the short length of the linker arm between the heterocyclic base and the site of attachment of the label (the end amino group) might influence the hybridization properties of the oligonucleotides. This would be especially the case if fluorescent moieties were to be attached since these tend to be large, planar molecules. A strategy was thus developed to introduce a longer linker arm on C-5. This is outlined in FIG. 4. The key compound 2 had its amino group deprotected with 95% $TFA/H_2O$, to give 8 in high yield. This was then allowed to react with the p-nitrophenyl ester 9, in the presence of one equivalent of 1,8-diazabicyclo[5.4.0]undec-7-ene (DBU), to give the adduct 10 in high yield. This product was converted into the phosphoramidite 11 in a similar manner to that described for 2.

EXAMPLE 7

Incorporation of modified nucleosides on the 5'-end of oligonucleotides

Initially, phosphoramidites 7 and 11 were tested by coupling them, manually, to the 5'-end of a preassembled oligonucleotide. Thus, the 30mer GGGCTTCACAA-CATCTGTGATGTCAGCAGG was assembled on an automated Applied Biosystems 380A DNA Synthesizer, and left on the resin, fully protected. This sequence is complementary to a region of the kallikrein mRNA that is common to all the kallikreins[15] and will be referred to as KPIB. The resin was transferred to a manual reaction cell. After detritylation of the last nucleoside, either 7 or 11 was coupled, in the presence of tetrazole. The couplings were essentially quantitative, as assayed by the trityl test. After removal of the phosphate protecting groups with thiophenoxide ion, the resin was treated with 90% TFA:10% ethanedithiol for five minutes, in order to remove the BOC protecting group. The presence of ethanedithiol protected with oligonucleotide from degradation. Triethylamine was used to neutralize the newly formed amino group and the secondary phosphates, and the oligonucleotide was then treated in the normal way to cleave it from the resin and remove the base protecting groups. The oligonucleotides were purified by polyacrylamide gel electrophoresis, with the modified oligonucleotides running one to two nucleotides slower than the normal KPIB.

Internal incorporation of modified nucleosides in oligonucleotides

Having established that the phosphoramidites 7 and 11 will couple as normal, we proceeded to synthesize oligonucleotides that incorporated these two modified nucleosides internally. The syntheses were carried out automatically on the Applied Biosystems DNA Synthesizer. Each of the phosphoramidites was used to synthesize two different oligonucleotides, one being KPIB, and the other the 40mer AGGTGCTCCAACCCCAATTG-CAGTTTGGGGGAACGTGTGA (HCAL). HCAL is complementary to part of the mRNA for human calcitonin and has been used to detect this mRNA in tissue sections[16]. The sequences were synthesized as shown, except that every thymidine residue was replaced with one of the modified nucleosides. the repetitive coupling yields were in the order of 99–100%. Following chain assembly, the oligonucleotide was treated sequentially with thiophenoxide ion, 90% TFA/ethanedithiol, cleaved from the solid support with concentrated ammonia solution and treated at 50° C. for 15 hr to remove the base protecting groups. When an attempt was made to analyse this product by polyacrylamide gel electrophoresis, no material could be seen on the gel by the normal method of UV shadowing. It appears that the presence of the amino groups, which would be charged at the pH of the gel medium, changes the electrophoretic properties of the oligonucleotide. Consequently, it was used in the next step without further purification. The repetitive coupling yields however are high, so that only a small amount of shorter sequences would be expected to be present in the product.

EXAMPLE 8

Coupling of fluorophores to the amino-oligonucleotides

The procedure used for the attachment of amine reactive fluorophores to amino-oligonucleotides is basically the same as that which has been widely used to attach such molecules to the ε-amino groups of lysine residues in proteins[17]. The procedure involves the reaction of the amino-oligonucleotide with the reactive fluorophore, at pH 9, so that a significant portion of the aliphatic amino groups are not protonareal. Smith et al. used a similar procedure in coupling fluorophores to 5'-aminothymidine containing oligonucleotides[1]. The labelling reaction mixture is put through a Sephadex G-25 column twice, to separate the excess unreacted dye from the oligonucleotide. The extent of labelling is subsequently determined by measuring the absorption of the product at 260 nm and at 495 nm. With the oligonucleotides containing the nucleotide from 7 (short C-5 arm) at the 5'-end, a single reaction using a 150 fold molar excess of FITC labelled 20% of the kallikrein oligonucleotide molecules and one third of the calcitonin ones. A second FITC coupling reaction on the same material increased the labelling to 67% and 83% respectively. This labelled material was also 5'-end labelled with [λ-$^{32}$P]ATP and subjected to electrophoresis. It showed a single radioactive band, at the expected position (data not shown).

The oligonucleotides containing the multiple internal primary aliphatic amino groups, and thus multiple potential sites of label incorporation were also subjected to the FITC coupling reaction. Firstly, the oligonucleotides containing the short C-5 arm are labelled. The kallikrein probe, containing seven potential sites of label incorporation, contained a single fluorescein per oligonucleotide molecule when the same labelling reaction as before was used, and the calcitonin probe, containing nine potential sites, contained 1.5 molecules of label. When the procedure was changed to using a much larger excess of FITC (900 fold), the level of incorporation was increased to 4.1 for KPIB and 7.2 for HCAL. These figures were calculated taking into account the absorbance of fluorescein at 260 nm, since this becomes significant when a number of fluorophores are attached to the oligonucleotide molecule. Repeating the reaction did not have any significant effect on the extent of labelling. In a test reaction, when normal KPIB was subjected to the labelling reaction with the large excess of FITC, it was found that a background level of labelling of 1 in 110 nucleotides was obtained. This compared with 15 per 110 nucleotides for the corresponding amino-oligonucleotides.

When the kallikrein oligonucleotide containing the nucleotide from 11 (long C-5 arm) at the 5'-end was labelled with a 900 fold excess of FITC, a single reaction gave complete incorporation of the label. This fluorescent product was also radioactively labelled at the 5'-end, and it gave a single band upon gel electrophoresis, at the expected position (data not shown).

When the oligonucleotides containing the multiple internal nucleotide substitutions carrying the long C-5 arm were subjected to the FITC coupling reaction, as before (large excess of FITC), the level of incorporation of label was 2.7 for KPIB and 5.2 for HCAL. These multi-labelled probes were also 5'-end labelled with (λ-$^{32}$P)ATP. Purification of the product mixture from the reaction on Sephadex G-25 gave a radioactive high molecular weight peak; however, on gel electrophoresis no radioactive band was seen.

EXAMPLE 9

Hybridization with the labelled oligonucleotides

Figure 5:
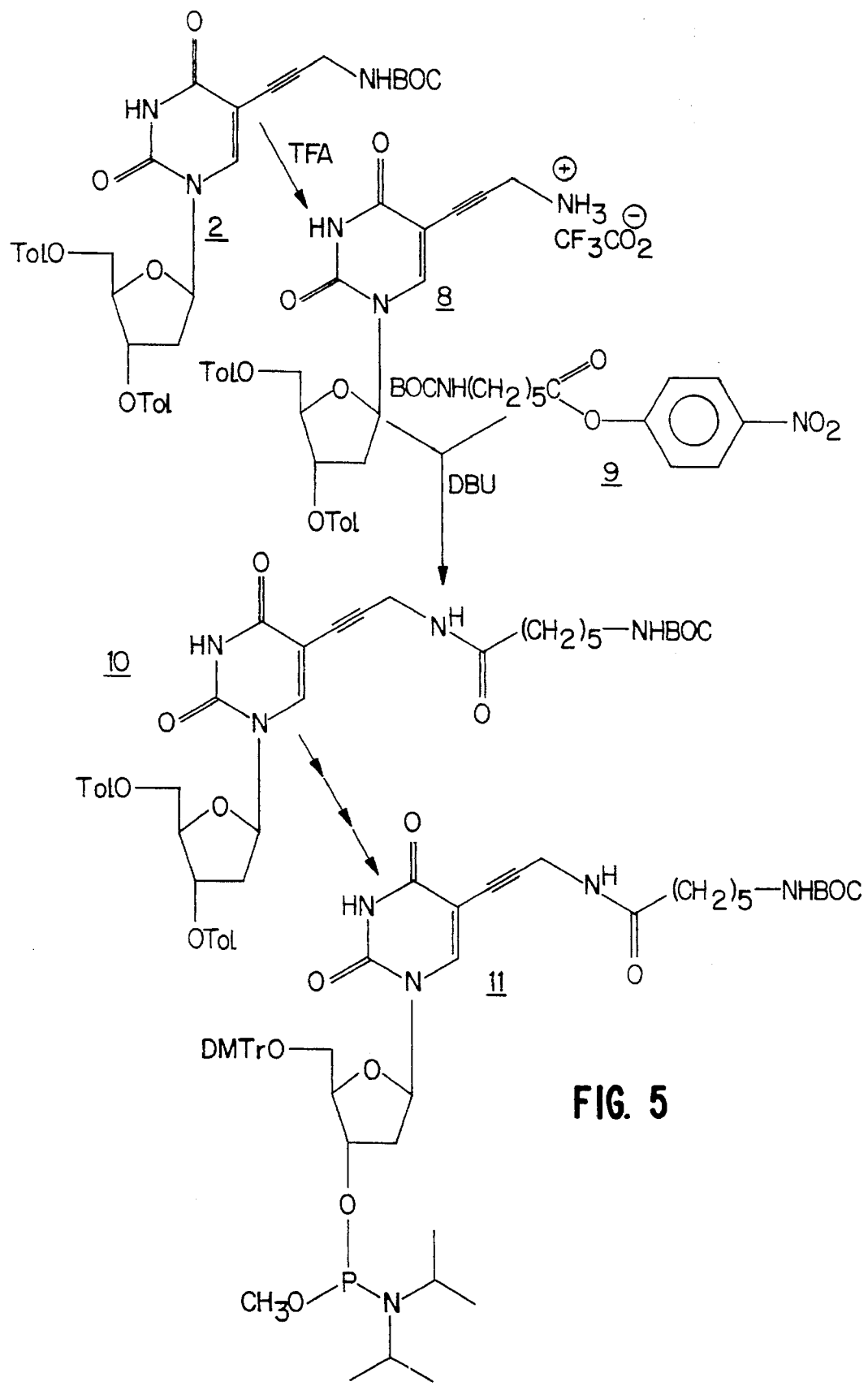
FIG. 5 shows the preparation of the long C-5 arm nucleoside phosphoramidate 11.
Figure 6A:
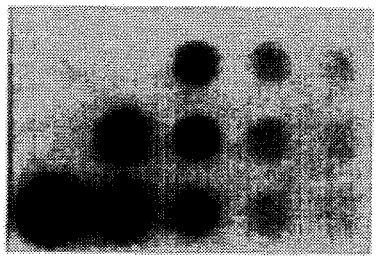
FIG. 6A shows a normal probe, high stringency conditions, 4 hr. exposure.
Figure 6B:
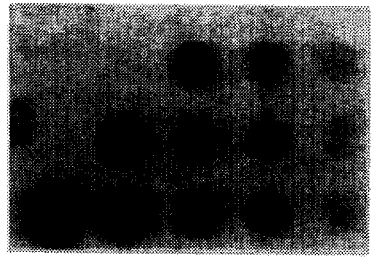
FIG. 6B shows a singly labelled probe, intermediate stringency, 4 hr. exposure.
Figure 6C:
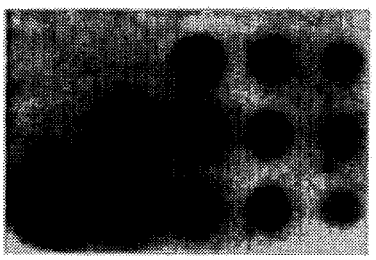
FIG. 6C shows a normal probe, high stringency, 16 hr. exposure.
Figure 6D:
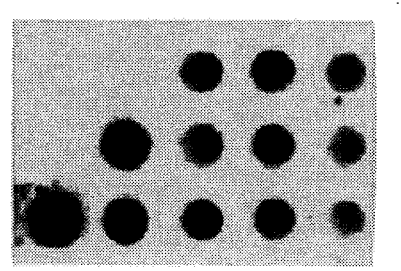
FIG. 6D shows a multi-labelled probe, low stringency 16 hr. exposure.
Figure 6E:
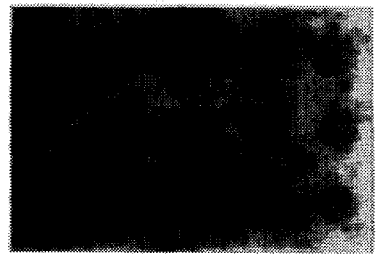
FIG. 6E shows a multi-labelled probe, lowest stringency, 16 hr. exposure.

The kallikrein oligonucleotides were tested for their ability to hybridize to mouse salivary gland Poly(A)$^+$ mRNA, which is rich in kallikrein message[15]. Poly(A)$^+$ mRNA was spotted on nitrocellulose filters, at varying concentrations, from 1 μg/per dot downwards. The fluorescent oligonucleotides were then 5'-end $^{32}$P labelled in the normal way and were used to probe the nitrocellulose filters. When the fluorescent oligonucleotides containing the short linker arm were used to probe the nitrocellulose filters, at high stringency, no signal was seen. However, when the conditions of intermediate stringency were used, the 5'-singly labelled probe gave a signal equal in intensity to that given by the normal unmodified probe (FIG. 5), whereas the multi-labelled probe still did not give any appreciable signal. When hybridizing under conditions of low and lowest stringency with the multi-labelled probe, the signal was ten times and three times less intense than that of the normal probe respectively.

These results also show that it is not a contaminating small amount of normal probe that is given rise to the hybridization signal, but the fluorescently labelled probe itself, otherwise a signal would be seen with the more stringent hybridization conditions as well.

When the fluorescent oligonucleotides containing the C-5 arm were hybridized, the singly labelled probe hybridized as well as the normal probe, under the high stringency conditions (FIG. 6). The multiply labelled probe, under these same conditions, gave a signal that was approximately three times weaker.

Figure 7C:
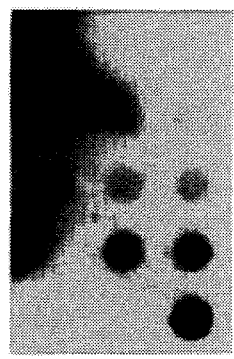
FIG. 7C shows a multi-labelled probe.
Figure 7B:
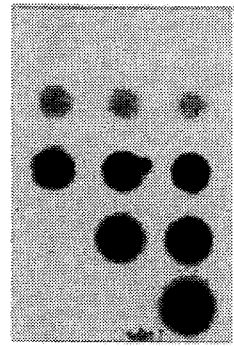
FIG. 7B shows a singly labelled probe.
Figure 7A:
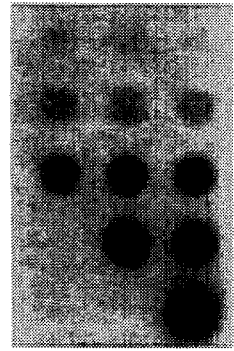
FIG. 7A shows a normal probe.
Figure 8B:
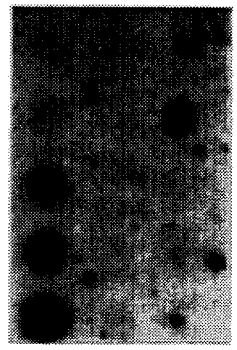
FIG. 8B shows a long C-5 arm probe.
Figure 8A:
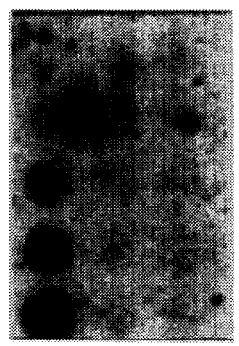
FIG. 8A shows a short C-5 arm probe.

The specificity of hybridization of the fluorescently labelled oligonucleotides was also checked. FIG. 7 shows the results of hybridization under conditions of intermediate stringency, of the two singly labelled (short and long arms) kallikrein oligonucleotides with liver mRNA and tRNA as compared to salivary gland mRNA. No visible signal is seen in the case of the non-kallikrein RNA containing nucleic acids indicating that the hybridization is specific to the kallikrein mRNA containing species.

REFERENCES

1. Smith, L. M., Fung, S., Hunkapiller, M. W., Hunkapiller, T. J., and Hood, L. E. (1985) Nucleic Acids Res. 13, 2439–2502.

2. Jablonski, E., Moomaw, E. W., Tullis, R. H. and Ruth, J. L. (1986) Nucleic Acids Res. 14, 6115–6128.

3. Ruth, J. L. (1984) DNA 3, 123.

4. Ruth, J. L., Morgan, C. and Pasko, A. (1985) DNA 4, 93.

5. Jablonski, E. and Ruth, J. L. (1986) DNA 5, 89.

6. Greene, T. W. (1981) Protective Groups in Organic Synthesis, John Wiley & Sons, Inc.

7. Barone, A. D., Tang, J. -Y. and Caruthers, M. H. (1984) Nucleic Acids Res. 12, 4051–4061

8. Rigby, P. J. W., Dieckmann, M., Rhodes, C., and Berg, P. (1977) J. Mol. Biol. 113:237–251

9. Taylor, P. M., Illmensee, R., and Summers, J. (1976) Biochim. Biophys. Acta 442:324–330

10. Caruthers, M. H., Beaucage, S. L., Eheavitim, J. W., Fisher, E. F., Goldman, R. A., de Hasetu, P. L., Manchecki, W., Mattkucci, M. D., Rosenthal, M. S., and Stabiusky, &. (1982) Cold Spring Harbor Sym. Quant. Bio. 47:411–418

11. Melton, D. A., Krieg, P. A., Rebagliati, M. R., Maniatis, T., Zinn, K., Green, M. R. (1984) Nucleic Acids Res. 12:7035–7056

12. Lowary, P., Sampson, J., Milligan, J., Groebe, D. and Ohlenbeck, O. C. (1986) "Structure and Dynamics of RNA, NATO ASI Series 110" pp. 69–76, ed. van Knippeuberg, P. H. and Hilbers, C. W., Plenum Press, New York 13. Still, W. C., Kahn, M. and Mitra, A. (1978) J. Org. Chem. 43, 2923–2925.

14. Tesser, G. I., Fischer, H. and Schwyzer, R. (1974) Helv. Chim. Acta 57, 1718–1730.

15. van Leeuwen, B. J., Evans, B. A., Tregear G. W. and Richards, R. I. (1986) J. Bio. Chem. 261, 5529–5535.

16. Zajac, J. D., Penschow, J., Mason, T., Tregear, G. W., Coghlan, J. P. and Martin, T. J. (1986) J. Clin. End. Metab. 62, 1037–1043.

17. Nairn, R. C. Fluorescent protein tracing, 4th Ed., Churchill Livingstone, Edinburgh, 1976.

18. Robins, M. J. and Bart, P. J. (1983) J. Org. Chem. 48, 1854–1862.

19. Sproat, S. and Bait, M. J. (1984) Oligonucleotide Synthesis (a practical approach), Bait, M. J. ed. pp. 83–116, IRL Press, Oxford 20. Penschow, J. D., Haralambidis, J., Aldred, P., Tregear, G. W. and Coghlan, J. P. (1986) Methods in Enzymology 124, 534–548

I claim:

1. A nucleoside of the formula (I):

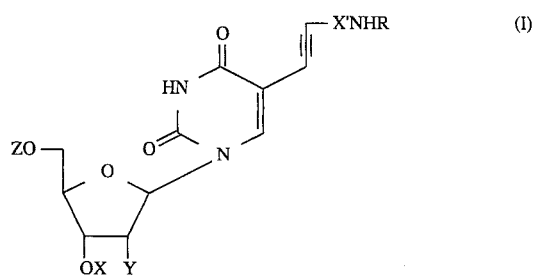

wherein (A) Y is H, OH or a protected hydroxy group;

(B) X is H, a phosphonate group or a phosphoramidite group of the formula

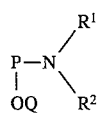

wherein (i) $R^1$ and $R^2$ are the same or different, and are selected from branched or unbranched $C_{1-30}$ alkyl or substituted $C_{1-30}$ alkyl having substituents selected from the group consisting of phenyl, benzyl, acyl, methyl, propyl, ethyl, isopropyl and butyl; and (ii) Q is a phosphate protecting group;

(C) Z is H, a phosphate group, a triphosphate group or a hydroxy-protecting group;

(D) X' is a branched or unbranched $C_{1-15}$ alkyl group;

(E) R is an acid labile amino protecting group, an amino reactive detectable marker, or the group

Y'NHA, wherein (i) Y' is a branched or unbranched $C_{1-40}$ alkyl carbonyl group; and (ii) A is an acid labile amino protecting group, or an amino reactive detectable marker.

2. A nucleoside as claimed in claim 1, wherein $R^1$ and $R^2$ are both isopropyl groups.

3. A nucleoside as claimed in claim 1 wherein X' is methylene and R is

CO(CH₂)ₙNHA, wherein A is an acid habile amino protecting group, or a detectable marker, and n is 5 to 15.

4. A nucleoside as claimed in claim 1, wherein

Y is H, OH or a protected hydroxy group;

X is

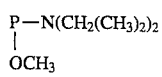

Z is dimethoxytrityl;

X' is CH₂; and

R is CH₂CO(CH₂)₅NHA, wherein A is an acid labile amino protecting group, or an amino reactive detectable marker.

5. A nucleoside as claimed in claim 1, wherein

Y is H, OH or a protected hydroxy group;

X is H;

Z is triphosphate;

X' is $CH_2$; and

R is $CO(CH_2)_5NHA$, wherein A is an acid labile amino protecting group, or an amino reactive detectable marker.

6. A nucleoside as claimed in any one of claims 1 to 5, wherein Q is selected from the group consisting of methyl, phenyl, substituted phenyl having substituents selected from the group consisting of halogen, hydroxy and $NO_2$ groups, benzyl, or cyanoethyl.

7. A nucleoside as claimed in any one of claims 1 to 5, wherein said non-radioactive detectable marker is selected from the group consisting of biotin, avidin, colloidal gold, colloidal silver and ferritin.

8. A nucleoside as claimed in any one of claims 1 to 5 wherein the amino reactive detectable marker is fluorescein.

9. A nucleoside as claimed in any one of claims 1 to 5, wherein the amino reactive detectable marker is a fluorophore precursor which contains one or more groups which suppress fluorescence, but which is capable of fluorescence once these groups are removed.

10. A nucleoside as claimed in claim 9, having the formula:

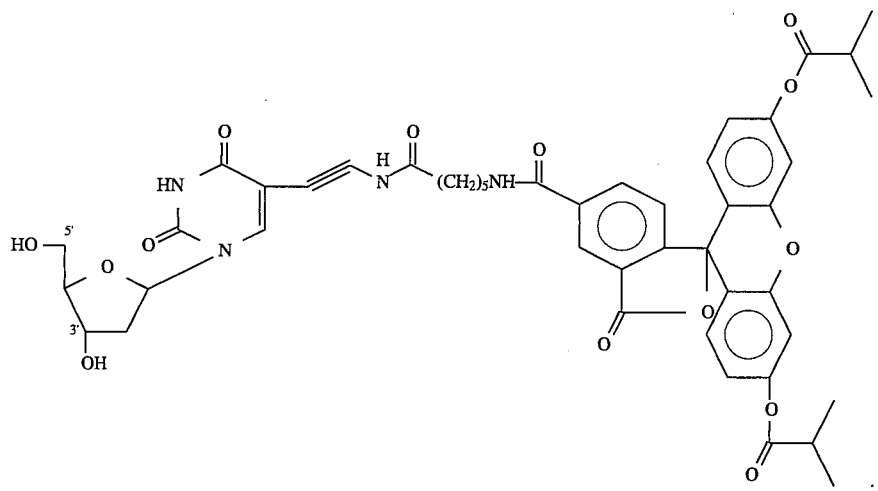

* * * * *